US010303337B2

(12) United States Patent
Teytelman et al.

(10) Patent No.: US 10,303,337 B2
(45) Date of Patent: May 28, 2019

(54) USER-POPULATED ONLINE REPOSITORY OF SCIENCE PROTOCOLS

(71) Applicants: Leonid Teytelman, Cambridge, MA (US); Alexei Stoliartchouk, Kensington, CA (US); Matthew Davis, Oakland, CA (US)

(72) Inventors: Leonid Teytelman, Cambridge, MA (US); Alexei Stoliartchouk, Kensington, CA (US); Matthew Davis, Oakland, CA (US)

(73) Assignee: Zappylab, Inc., Kensington, CA (US)

( * ) Notice: Subject to any disclaimer, the term of this patent is extended or adjusted under 35 U.S.C. 154(b) by 106 days.

(21) Appl. No.: 15/675,143

(22) Filed: Aug. 11, 2017

(65) Prior Publication Data

US 2017/0364216 A1  Dec. 21, 2017

Related U.S. Application Data

(63) Continuation of application No. 13/946,685, filed on Jul. 19, 2013, now abandoned.

(60) Provisional application No. 61/673,624, filed on Jul. 19, 2012, provisional application No. 61/776,472, filed on Mar. 11, 2013.

(51) Int. Cl.
*G06F 3/048* (2013.01)
*G06F 3/0482* (2013.01)
*G06F 16/00* (2019.01)
*G06F 19/00* (2018.01)

(52) U.S. Cl.
CPC ............ *G06F 3/0482* (2013.01); *G06F 16/00* (2019.01); *G06F 19/00* (2013.01); *G06F 19/325* (2013.01)

(58) Field of Classification Search
CPC ....................................... G06F 3/0481–3/0489
See application file for complete search history.

(56) References Cited

U.S. PATENT DOCUMENTS

| 6,915,254 | B1 | 7/2005 | Heinze et al. |
| 7,584,019 | B2 | 9/2009 | Feingold et al. |
| 7,610,192 | B1 | 10/2009 | Jamieson |
| 7,853,446 | B2 | 12/2010 | Allard et al. |
| 8,417,537 | B2 | 4/2013 | Apacible et al. |

(Continued)

FOREIGN PATENT DOCUMENTS

WO  WO 2012/019046  2/2012

OTHER PUBLICATIONS

U.S. Appl. No. 61/673,624, Teytelman et al.
U.S. Appl. No. 61/776,472, Teytelman et al.

*Primary Examiner* — Steven B Theriault
(74) *Attorney, Agent, or Firm* — Gary J. Gershik; Cooper & Dunham LLP

(57) ABSTRACT

Systems, apparatus and methods are provided to maintain a user-populated online repository of science protocols. A user may create a science protocol by inputting information relating to one or more steps of an experiment. The created science protocol may be stored in the protocol database. A user may search the protocol database using a navigable menu for accessing a plurality of application functionalities associated with the protocol database. Based on the search, a user may be able to retrieve and download the created science protocol. The user may be able to modify and/or annotate the created science protocol. The modified and/or annotated science protocol may be stored in the protocol database as a modified and/or annotated version of the created science protocol.

8 Claims, 14 Drawing Sheets

(56) References Cited

U.S. PATENT DOCUMENTS

| | | |
|---|---|---|
| 8,572,507 B2 | 10/2013 | Abrams et al. |
| 2001/0032210 A1 | 10/2001 | Frank et al. |
| 2001/0049681 A1 | 12/2001 | Bova |
| 2002/0078016 A1 | 6/2002 | Lium et al. |
| 2002/0128734 A1 | 9/2002 | Dorsett, Jr. |
| 2002/0198739 A1 | 12/2002 | Lau et al. |
| 2003/0088363 A1 | 5/2003 | Aronow |
| 2004/0117206 A1 | 6/2004 | Steinberger et al. |
| 2004/0243614 A1 | 12/2004 | Boone et al. |
| 2005/0013736 A1 | 1/2005 | McKeever |
| 2005/0044110 A1 | 2/2005 | Herzenberg et al. |
| 2005/0273475 A1 | 12/2005 | Herzenberg et al. |
| 2006/0020444 A1 | 1/2006 | Cousineau et al. |
| 2006/0020466 A1 | 1/2006 | Cousineau et al. |
| 2006/0052940 A1 | 3/2006 | Shi |
| 2007/0055926 A1 | 3/2007 | Christiansen et al. |
| 2008/0010341 A1 | 1/2008 | Curtis et al. |
| 2009/0222746 A1 | 9/2009 | Chirica et al. |
| 2009/0259321 A1 | 10/2009 | Stellari et al. |
| 2009/0316977 A1 | 12/2009 | Juncker et al. |
| 2010/0080427 A1 | 4/2010 | Yeluri et al. |
| 2010/0169365 A1 | 7/2010 | Chupp et al. |
| 2010/0323336 A1 | 12/2010 | Guimaraes |
| 2011/0231758 A1 | 9/2011 | DeSimas et al. |
| 2012/0123997 A1 | 5/2012 | Boonyaratanakornkit et al. |
| 2012/0212337 A1 | 8/2012 | Montyne et al. |
| 2012/0215557 A1 | 8/2012 | Flanagan et al. |
| 2012/0278102 A1 | 11/2012 | Johnson |
| 2013/0219265 A1 | 8/2013 | Nalabolu |
| 2014/0026080 A1 | 1/2014 | Teytelman et al. |
| 2014/0188545 A1 | 7/2014 | Chirica et al. |

| STEP | DESC. | RGNT | AMT | TIME |
|---|---|---|---|---|
| 1 | fixation | formald. | 5µl | 30min |
| 2 | spin | - | 3000rpm | 5min |
| 3 | wash | BufferB | 1ml | - |
| 4 | spin | - | 3000rpm | 3min |
| 5 | digest | Zymolyase | 1µl | 60min |
| 6 | wash | BufferB | 1ml | - |
| 7 | spin | - | 2000rpm | 5min |
| 8 | precip. | 100% ethan. | 1ml | 24hrs |

Call   End

Fig. 2C

| STEP | DESC. | RGNT | AMT | TIME |
|---|---|---|---|---|
| ✓ 1 | fixation | formald. | 5μl | 30min |
| 2 | spin | - | - | 3000rpm 5min |
| 3 | wash | BufferB | 1ml | - |
| 4 | spin | - | - | 3000rpm 3min |
| 5 | digest | Zymolyase | 1μl | 60min |
| 6 | wash | BufferB | 1ml | - |
| 7 | spin | - | - | 2000rpm 5min |
| 8 | precip. | 100% ethan. | 1ml | 24hrs |

Call | End

Fig. 2D

| STEP | DESC. | RGNT | AMT | TIME |
|---|---|---|---|---|
| 1 | fixation | formald. | 5μl | 30min |
| 2 | spin | - | 3000rpm | 5min |
| 3 | wash | BufferB | 1ml | - |
| 4 | spin | - | 3000rpm | 3min |
| 5 | digest | Zymolyase | 1μl | 60min |
| 6 | wash | BufferB | 1ml | - |
| 7 | spin | - | 2000rpm | 5min |
| 8 | precip. | 100% ethan. | 1ml | 24hrs |

Call | End

USER-POPULATED ONLINE REPOSITORY OF SCIENCE PROTOCOLS

CROSS-REFERENCE TO RELATED APPLICATIONS

This application is a continuation of U.S. Ser. No. 13/946,685, filed Jul. 19, 2013, which claims priority of U.S. Provisional Application Nos. 61/776,472, filed Mar. 11, 2013, and 61/673,624, filed Jul. 19, 2012, the contents of which are hereby incorporated by reference.

TECHNICAL FIELD

This disclosure relates to tools, such as systems, apparatuses, methodologies, computer program products, etc., for providing a user-populated online repository of science protocols.

BACKGROUND

In the field of biomedical sciences, chemistry, medicine and other related disciplines, protocols are used to record or document laboratory experiments. However, there has been no easy way of managing a plurality of such protocols, and similarly, no convenient way of publishing or sharing such protocols.

There have been many attempts at creating a protocol repository over the past years. However, all have failed because of the impossible task of reaching out to laboratories and manually entering one protocol at a time.

There is a need for a more convenient way of building and maintaining a protocol repository.

SUMMARY

This disclosure provides tools (in the form of apparatuses, methodologies and systems) for allowing users to create and edit science protocols, upload such science protocols onto an online protocol repository, and download science protocols uploaded by other users from the online protocol repository.

In an aspect of this disclosure, a repository apparatus provides a user registration function to register a user, a protocol submission function to register a specific protocol in a protocol database, and a protocol search function to search the protocol database based on specified key words and search options.

In another aspect of this disclosure, an application user interface apparatus includes a creation part configured to provide a protocol creation user interface, receive a series of user inputs entered by the user through the protocol creation user interface, create a new protocol based on the series of user inputs, and add the new protocol to a local protocol database, a modification part configured to provide a protocol modification user interface, receive a user selection of a specific protocol of the plurality of protocols and a series of user inputs entered by the user through the protocol modification user interface, and modifying the specific protocol based on the series of user inputs. All output part configured to provide a protocol output user interface, receive a user selection of a specific protocol of the plurality of protocols and a destination specified by the user, and outputting the specific protocol to the specified destination, and a download part configured to allow the user to (i) download a protocol from the protocol database by communicating with the repository apparatus or (ii) import a protocol from a text file or e-mail.

In another aspect of this disclosure, a system provides a web-based repository of science protocols. The system may comprise a repository apparatus configured to execute a protocol management application that includes a plurality of application functionalities, the application functionalities including: a user registration function to register a user, a protocol submission function to register a specific protocol in a protocol database, and a protocol search function to search the protocol database based on specified keywords and search options. The repository apparatus may include a web interface part configured to provide a user with navigable menu for accessing the plurality of application functionalities. The system may further include an application user interface apparatus configured to communicate with the protocol management application, the application user interface apparatus including a processor and a non-transitory storage medium embodying instructions executable by the processor to configure the application user interface apparatus to include: a creation part configured to provide a protocol creation user interface, receive a series of user inputs entered by a user through the protocol creation user interface and create a new protocol based on the series of user inputs, a modification part configured to provide a protocol modification user interface, receive a user selection of a specific protocol of the plurality of protocols and a series of user inputs entered by a user through the protocol modification user interface, and modify the specific protocol based on the series of user inputs; an output part configured to provide a protocol output user interface, receive a user selection of a specific protocol of the plurality of protocols and output the specific protocol to one or more destinations; and a download part configured to allow the user to (i) download a protocol from the protocol database by communicating with the repository apparatus or (ii) import a protocol from a text file or e-mail to the repository apparatus.

In another aspect of this disclosure, a protocol management apparatus may be provided including a processor and a non-transitory storage medium embodying instructions executable by the processor to configure the application user interface apparatus to include: a creation part configured to provide a protocol creation user interface, receive a series of user inputs entered by a user through the protocol creation user interface, create a new protocol based on the series of user inputs, and add the new protocol to a protocol database; a modification part configured to provide a protocol modification user interface, receive a user selection of a specific protocol of the plurality of protocols and a series of user inputs entered by a user through the protocol modification user interface, and modify the specific protocol based on the series of user inputs; an output part configured to provide a protocol output user interface, receive a user selection of a specific protocol of the plurality of protocols and output the specific protocol to the one or more destinations; and a display part configured to display a list of the plurality of protocols stored in the protocol database.

In another aspect of this disclosure, a processor-implemented method for providing a web-based repository of science protocols may be provided. The method may comprise providing a protocol database for containing a plurality of scientific protocols; allowing one or more users to create one or more scientific protocols; storing the one or more created scientific protocols in the protocol database; allowing the one or more users to search of the protocol database by using a navigable menu for accessing a plurality of application functionalities associated with the protocol database; retrieving the one or more created scientific protocols from the protocol database based on the search; and allowing the one or more users to view or download the one or more created scientific protocols.

The method may further comprise allowing the one or more users to annotate the one or more created scientific protocols by submitting one or more annotations to the one or more created scientific protocols; and storing the one or more annotations to the one or more created scientific protocols in the protocol database.

According to one embodiment, each of the one or more annotations to the one or more created scientific protocols in the protocol database are separately stored as additional entries associated with the one or more created scientific protocols.

The method may further comprise allowing one or more users to conduct one or more additional searches of the protocol database by using a navigable menu for accessing a plurality of application functionalities associated with the protocol database; retrieving one or more annotated scientific protocols from the protocol database based on the one or more additional searches; and allowing one or more users to view or download the one or more annotated scientific protocols from the protocol database.

According to one embodiment, the one or more annotated scientific protocols are displayed in addition to one or more originally created scientific protocols.

The method may further comprise allowing a protocol management application to communicate with a lab device to automatically configure the lab device based on the one or more created scientific protocols or based on the one or more annotated scientific protocols.

The method may further comprise allowing a protocol management application to communicate with a lab device to monitor a status of the lab device based on the one or more created scientific protocols or based on the one or more annotated scientific protocols.

BRIEF DESCRIPTION OF THE DRAWINGS

The aforementioned and other aspects, features and advantages can be better understood from the following detailed description with reference to the accompanying drawings wherein:

FIG. 2C-2E show sample screens of protocol tracking, according to an exemplary embodiment;

FIG. 2F shows a sample screen showing annotations, according to an exemplary embodiment;

DETAILED DESCRIPTION

Figure 1:
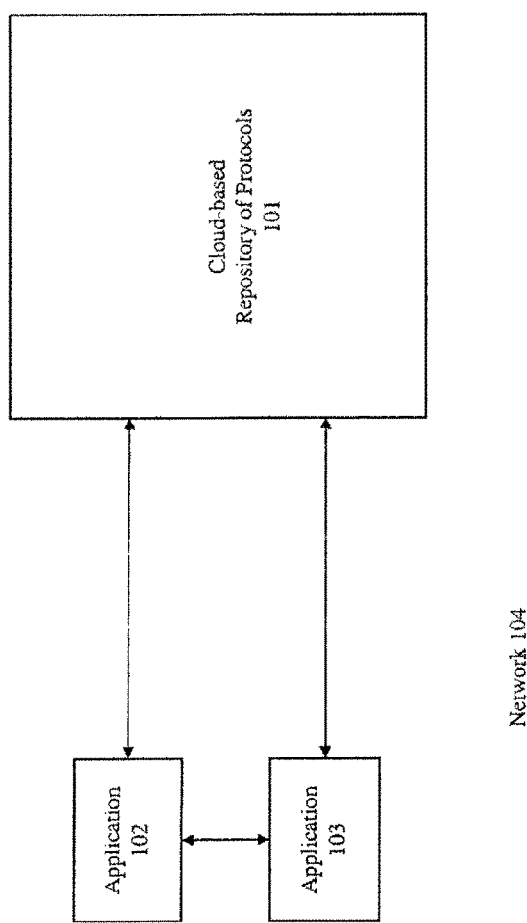
FIG. 1 shows a block diagram of a system, according to an exemplary embodiment.

This disclosure provides tools (in the form of apparatuses, methodologies and systems) for allowing users to access a web-based repository of science protocols. Such service can be provided through a web-based server via the Internet. In other embodiments, the server need not be a web-based server and may comprise any type of server. Likewise, in other embodiments, the service may be provided through other means besides via the Internet.

In describing examples and exemplary embodiments illustrated in the drawings, specific terminology is employed for the sake of clarity. However, this disclosure is not intended to be limited to the specific terminology so selected, and it is to be understood that each specific element includes all technical equivalents that operate in a similar manner.

Referring now to the drawings, wherein like reference numerals designate identical or corresponding parts throughout the several views, FIG. 1 shows a block diagram of a system 100, according to an exemplary embodiment of the present disclosure. The system 100 includes a cloud-based repository of protocols 101, applications 102 and 103 and a network 104 through which the repository 101 and the applications 102 and 103 communicate. Those skilled in the art will appreciate that the repository needs not be cloud-based but can comprise any type of repository of protocols while remaining within the scope of the current disclosure.

As used herein, the term repository apparatus may include, but is not limited to, a processor and a storage medium. The repository apparatus' storage medium may contain a protocol management application executable by the processor.

The cloud-based repository of protocols 101 may include free, up-to-date and evolving protocols in biomedical sciences, chemistry, medicine, and other disciplines. A social network layer will enable scientists to connect by expertise, with geographically proximal option, to troubleshoot the use of similar techniques. The social network layer may enable scientists to connect based on various criteria, such as expertise, geographic proximity, profession, research collaboration, etc.

The repository 101 may be accessible by users on a web site via a web interface that includes a menu for allowing the users to navigate to different parts of the website. The web site may include the protocol repository as well as other sections such as news, jobs and/or publications. The website preferably includes links to a login screen, FAQ (frequently asked questions) and contacts.

The pages of the web site may have two different states: one for anonymous users and another for logged-in registered users. The web site may also include further states for users such as system administrators.

The protocol repository page may include an index providing quick navigation into a particular scientific domain. The users may also search the protocol database by keywords and/or filter by reagents, type of protocol and/or scientific domain.

On a page for a particular protocol, the protocol is preferably displayed with the author's name and the dates of creation and last revision.

Users may vote up or vote down a particular protocol, and the repository may maintain a running score (i.e. rating) for each of the protocols. For example, a protocol with a high rating may be shown before another protocol with a lower rating. The users may also flag a particular protocol as spam or share the particular protocol with other users, for example, via e-mail or other social networking web site. Access to such features may be limited to logged-in registered users.

The web site may also include a notification feature in which a notification is sent to any users who have downloaded a particular protocol when the particular protocol is modified by the author (or another user) of the protocol.

The web site preferably allows users to upload a protocol, either through an application (e.g. the application 102) or a web browser on a terminal device (e.g. a desktop), or by way of any other means of uploading. When such a protocol is uploaded to the online protocol repository (i.e. repository 101), the protocol (or protocol steps thereof) may be associated with other protocols existing on the protocol repository and/or publications with citation information (e.g. journal, author, date, manuscript title).

The web site may also allow the users to create protocols in a manner similar to that discussed infra in connection with the application 102.

The website preferably has a way of standardizing protocol submission. For example, when a protocol is uploaded or created, the steps in the protocol may be checked and/or edited to improve consistency and/or aid in automated categorization and comparison of submissions (e.g. if a step is described as "spin" or "centrifugation", all such terms will be changed to "spin"). Alternatively or additionally, the web site may also implement and/or enforce certain guidelines upon user submission of protocols and/or reject non-complying protocols rather than accepting the protocols and automatically editing the accepted protocols.

The web site may also include a feature for automatically flagging protocol discrepancies and/or identifying variable steps in each protocol, based on comparison of submitted instances (i.e. steps). This feature may allow scientists to trouble-shoot, optimize, and/or sample different parameters when adopting any protocol to their particular lab and/or use.

The web site may also have a feature for displaying new published manuscript suggestions based on the one or more type of protocols and/or other publications that a particular registered user may have searched. Similarly, based on the registered user's history of searches, refined and ranked search results of scientific literature may be displayed to the registered user.

Returning to the system 100 of FIG. 1, the application 102 may allow an application user to perform a variety of tasks related to protocol management. For example, the application 102 may allow the application user to create a new protocol entry. The application user may be asked to input each step of an experiment using a user interface (e.g. text fields including sequential step number, step name, duration, reagent, amount, description and warning/reminder). The sequential step number is preferably automatically entered and/or automatically incremented. All user-entered fields are optional, and each protocol preferably has a unique name.

The application user may also import a protocol from a source, for example, a CSV (comma separated values) file. In addition, the application user may also use an e-mail containing a properly formatted text (either in the body of the e-mail or as an e-mail attachment) to import a protocol. In some embodiments, the imported protocol is stored in a personal protocol database, which may be implemented using a local memory device and/or via a network (e.g. cloud storage of the application user). In other embodiments, the imported protocol may be stored in any other type of storage medium.

Additionally, the application user may download a protocol from a web-based protocol repository (e.g. the cloud-based repository of protocols 101 of FIG. 1). In order to download a protocol from the web-based protocol repository, the application user is preferably required to enter login credentials recognized by the protocol repository management system managing the repository.

Figure 2A:
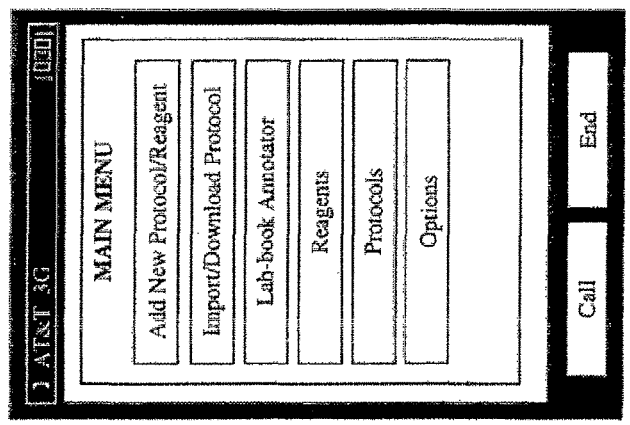
FIG. 2A shows a sample menu screen, according to an exemplary embodiment.
Figure 2B:
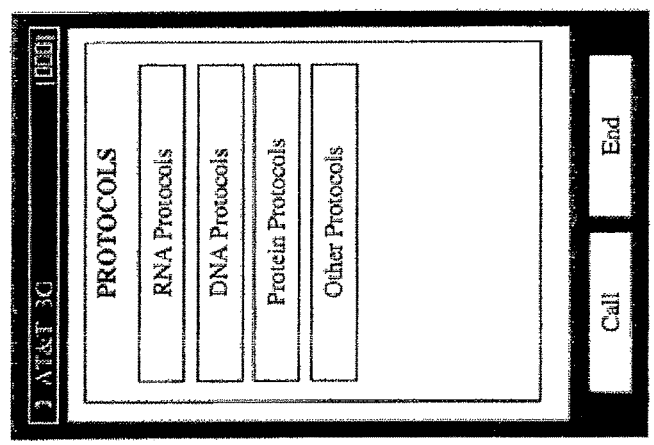
FIG. 2B shows another sample menu screen, according to an exemplary embodiment.

The protocols that are created, imported and/or downloaded are preferably organized under folders and/or headings that are user-specified and/or automatically generated based on the nature of the protocols. For example, headings such as "RNA Protocols", "DNA Protocols" and "Protein Protocols" may be used, as shown in FIG. 2B. The user-created protocols may also be organized separately from the imported/downloaded protocols.

In some embodiments, the user can also specify and cause the application 102 to maintain at least one separate section for favorite and/or frequently-used protocols (or reagents discussed below).

The application user may also modify and/or annotate the protocols stored in the personal, protocol database or other type of protocol database. For example, a prolonged touch of a given step (i.e. row) may open a text edit field for allowing the user to provide modifications and/or annotations to the existing, stored protocol.

In some embodiments, the user may submit one or more annotations to an existing stored protocol. In this embodiment, the user would submit the annotated information as an additional layer to the existing protocol. Thus, the one or more annotations can be saved as additional layers to the existing, stored protocol, with the ability to export a record of the entire experiment (i.e. annotated protocol), step-by-step. For example, if a user provides an annotation for several steps of the existing stored protocol, each of those annotations can be stored separately for each step of the experiment. In some embodiments, the changes and/or annotations may be indented and displayed underneath the respective step in the originally created protocols. In such embodiments, the annotated protocols may be stored in the protocol database as annotated versions of the originally created protocols. Thus, when a user later obtains or downloads an annotated protocol, for example, from the protocol database, the user will see the originally created protocol along with the tracked annotations made thereto. Those annotations can be designated in such a way so that it is readily apparent that they are additions made by one or more users. According to one embodiment, the one or more annotations may be displayed in any form sufficient to indicate that they are annotations and/or modifications to the originally created protocol, for example, in the form of underlining, indenting, designations as "annotations" in a separate section in connection with each respective step, or any other type of display sufficient to indicate that the information is annotated information.

It should be readily apparent to one of ordinary skill in the art that there are one or more users using the system of the present invention. If several users make one or more annotations to any given protocol, each of the annotations made by each user can be separately stored in the protocol database and can be indented and displayed underneath each respective step in the originally created one or more protocols.

According to an embodiment, the author and/or entry date of each of the one or more annotations may also be visible to the user. Such information may assist the user in deciding when to follow a step as written by the original author and when to follow a step as written by a subsequent author. As a result, the disclosed application provides a user with the ability to instantly see all modified and optimized changes for a given step of a given protocol.

In some embodiments, user-submitted modifications and/or annotations to the protocols may be stored as separate, modified protocol entries in the protocol database. Thus, when a user saves the one or more modified protocols, the user is submitting separate modified protocols, with the repository now storing two or more versions, both the original protocol and the modified protocols. In turn, when one or more users later searches for the protocol, the protocol database may retrieve at least two search results: the original protocol and at least one modified protocol. As a result, for a given protocol, the disclosed application provides users with various options of the protocol to follow. For example, users may decide to download a particular modified protocol because it is the most current or has received the highest user rating compared to other modified protocols generated by the search. Alternatively, users may instead decide to download the original version of the protocol because it was written by a notable professor.

In some embodiments, user-submitted modifications and/or annotations to the published protocols may operate to overwrite the existing protocol. In such cases, the protocol database may store the modified protocol by replacing an existing protocol with an updated protocol that includes the modifications and/or annotations. In turn, when an application user later searches for the protocol after it has been modified and/or annotated, the most current and up-to-date modified protocol will be provided to the application user.

Additionally, data relating to reagents (e.g. substance or compound used in the protocols) can also be created, imported and downloaded in a similar manner. The reagents are preferably tagged as "reagents" and may be stored and displayed separately from the protocols. The reagents can also be directly (or indirectly) linked to the "reagent field" of any protocol. For example, when creating a new protocol, to populate the reagent field of the protocol, the user may be able to select from a list of reagents currently stored in the personal reagent database, for example, using a drop-down option.

When going through an experiment, a prolonged touch of a reagent displayed, for example, on a mobile screen should bring up the reagent's recipe, if such recipe has been entered.

Also, the application user can select a protocol to run (i.e. to conduct the experiment). When the user selects the protocol to run, the protocol instance becomes a record of the particular execution on that day, thus acting as a digital lab notebook. In addition, the application 102 may display a checklist of all the steps included in the protocol, and the application user may be able to check off each step as he or she completes the step. For example, as shown in FIGS. 2C-2E, the user may be able to check off the checkboxes associated with the steps as he or she completes each step. For example, the application 102 may alert the user when it is time to move onto the next step (e.g. 30 minutes after step 1 is started).

Figure 2F:
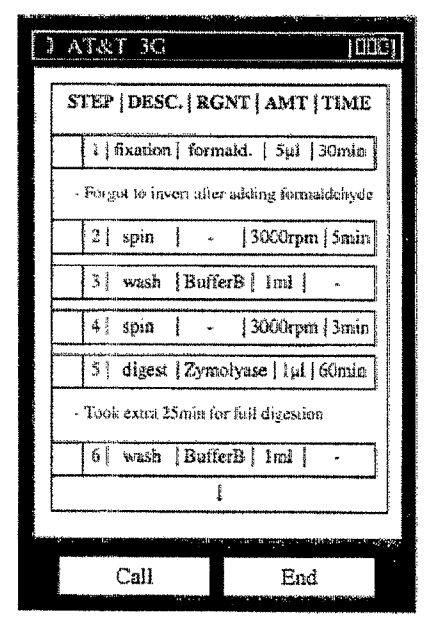
Figure 2G:
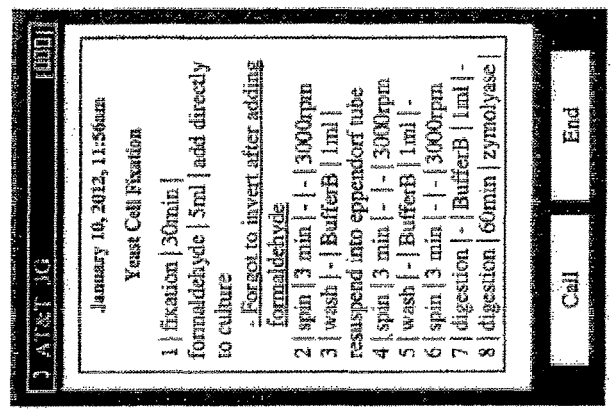
FIG. 2G shows another sample screen showing annotations, according to another exemplary embodiment.
Figure 2H:
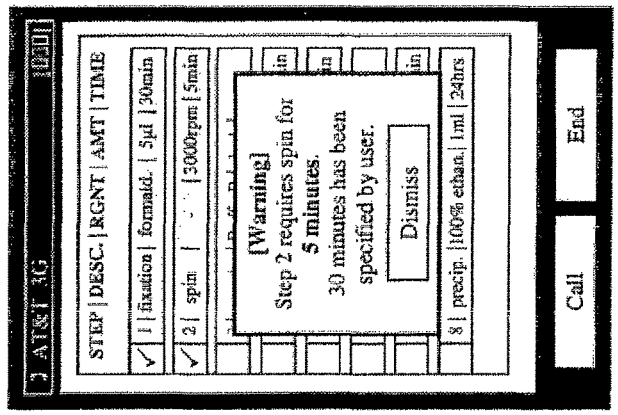
FIG. 2H shows a sample message displayed to the user, according to another exemplary embodiment.
Figure 2I:
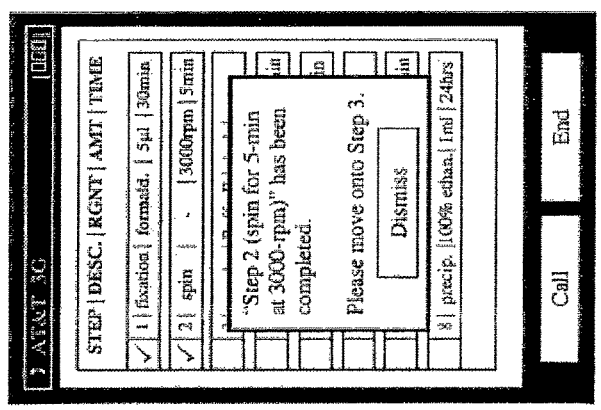
FIG. 2I shows a sample message displayed to the user, according to another exemplary embodiment.

The application 102 may also interface with laboratory equipment for automatic notifications and/or error checking. For instance, if a centrifugation step requires a 10-minute spin according to the protocol in the application 102, and the user attempts to activate the centrifuge for 30 minutes, the application 102 will display a warning (e.g., indicating that the user attempt deviates from the protocol, such as shown in FIG. 2H). In some embodiments, an application may be configured (e.g., via a user configuring a Settings feature) to display a warning for some but not all deviations between a user's equipment input and an application's protocol. For example, the application may be configured to warn the user, only if the protocol and/or step of the protocol was created and/or modified by an author with a predetermined level of trustworthiness (e.g., by a Professor at a University, by a scientist who is part of a well-respected research collaboration, etc.). Data indicative of authors' trustworthiness may be stored in the repository. In some embodiments, data indicative of authors' trustworthiness is safeguarded (e.g., by a system administrator and/or by entry of the author's credentials) in order to preserve the integrity of such information in the repository. In some embodiments, the application may be configured to warn the user if the protocol and/or step of the protocol was authored and/or modified by another entity participating in the user's research collaboration, to thereby help ensure continuity throughout the collaboration. In some embodiments, the application may be configured to warn the user only if the protocol received a user score (e.g., a user rating) above a predetermined threshold. In some embodiments, the application may be configured to warn the user only if the user's equipment input differs from the protocol by a predetermined amount (e.g., only if the time in the centrifuge differs by more than 5 minutes). In some embodiments, lab devices may be configured to communicate with the application. For example, lab equipment may be configured to send a notification to the application indicating that a status of the lab equipment has changed. For example, the centrifuge may communicate to the application 102 when the spin is finished, with the alert transmitted to the user (e.g., notifying the user that he or she is ready to move onto the next step, such as shown in FIG. 2I). Further, if the protocol specifies the settings (e.g. speed, temperature, time, etc.) for the laboratory equipment to be used for a particular step, the application 102 may communicate with the laboratory equipment to cause such settings to be automatically loaded onto the laboratory equipment. Thus, in an exemplary embodiment, when the application user initiates a centrifugation step requiring a 10-minute spin, the application 102 automatically configures the centrifuge to be activated for 10 minutes. In some embodiments, an application may be configured (e.g., via a user Settings feature) to automatically configure laboratory equipment for some but not all instances. For example, in some embodiments, the application may be configured to automatically configure laboratory equipment only if the protocol and/or step of the protocol was created and/or modified by an author with a predetermined level of trustworthiness. In some embodiments, the application may be configured to automatically configure laboratory equipment if the protocol and/or step of the protocol was authored and/or modified by another entity participating in the user's research collaboration, to thereby help ensure continuity throughout the collaboration. In some embodiments, the application may be configured to automatically configure laboratory equipment only if the protocol has received a user score (e.g., a user rating) above a predetermined threshold. In some embodiments, the application may be configured to automatically configure certain pre-selected laboratory equipment and not automatically configure other pre-selected laboratory equipment.

Figure 5:
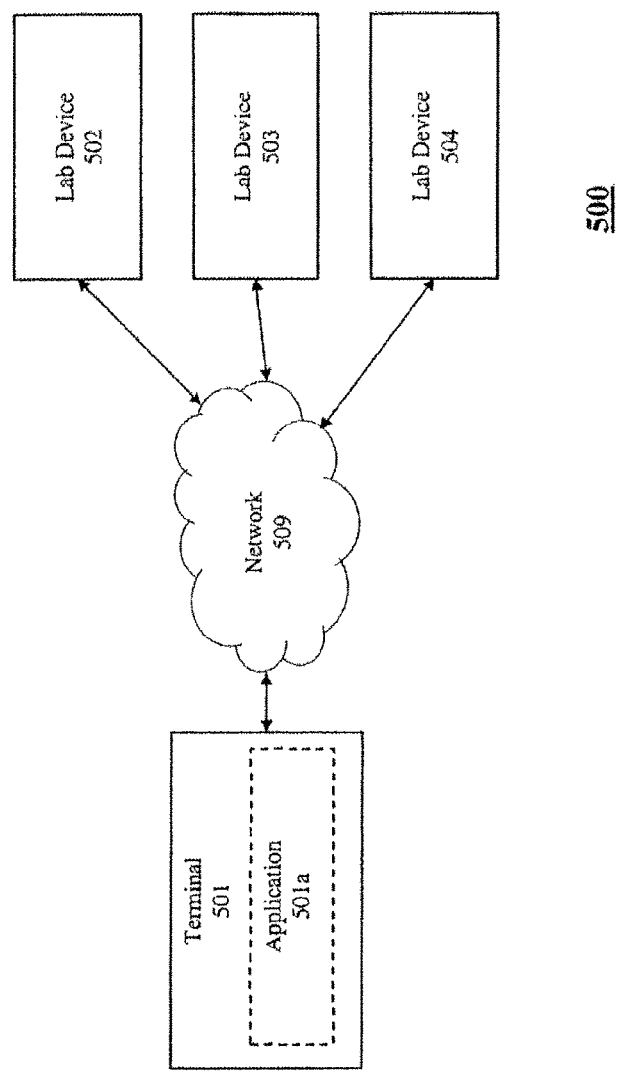
FIG. 5 shows a block diagram of a system, according to another exemplary embodiment.

For example, FIG. 5 shows a block diagram of a system, according to an exemplary embodiment. As shown in FIG.

5, an application 501a is running on a terminal 501, and the terminal 501 communicates with lab devices 502-504 via a network 509.

The operation of the application 501a is similar to that of the application 102 described supra with reference to FIG. 1.

The network 509 can be a local area network, a wide area network or any type of network such as an intranet, an extranet (for example, to provide controlled access to external users, for example through the Internet), the Internet, etc., or a combination thereof. Further, other communication links (such as a virtual private network, a wireless link, etc.) may be used as well for the network 509. In addition, the network 509 preferably uses TCP/IP (Transmission Control Protocol/Internet Protocol), but other protocols such as SNMP (Simple Network Management Protocol) and HTTP (Hypertext Transfer Protocol) can also be used. How devices can connect to and communicate over networks is well-known in the art and is discussed for example, in "How Networks Work", by Frank J. Derfler, Jr. and Les Freed (Que Corporation 2000) and "How Computers Work", by Ron White (Que Corporation 1999), the entire contents of each of which are incorporated herein by reference.

It should be appreciated that although one terminal and three lab devices are shown in FIG. 5, the system 500 is not limited to such configuration and may include any arbitrary number of terminals and lab devices.

In addition, each step of a protocol may also be expanded to display a detailed view of the step. Any changes and/or annotations previously made to a particular step may be displayed along with the particular step, as shown in FIG. 2F. In another exemplary embodiment, the annotator may have a view as illustrated in FIG. 2G. The application user may be allowed to change and/or annotate the steps directly on the application. Several protocol instances can be tracked in the above manner concurrently (that is, two or more protocols may be tracked in parallel in the application).

When the application user first opens the application 102, the user may see a menu screen for navigating through different functionalities of the application. For example, as shown in FIG. 2A, the menu screen may include a plurality of buttons for allowing the user to access the various functionalities of the application.

In addition, in some embodiments, the application user may also export and/or upload the protocols and/or reagents stored in the personal database or in another type of database. Such protocols and/or reagents can be exported and/or uploaded through any means such as by e-mailing the protocols and/or reagents to another user, transferring the protocols and/or reagents to another application user, and/or uploading the protocols and/or reagents to the web-based protocol repository.

As shown in FIG. 1, the applications 102 and 103 may also communicate to exchange protocols and/or reagents, for example, using the import/export feature of the application.

Although only two applications are shown in FIG. 1, it should be understood that the system 100 can include a plurality of other applications (which can have similar or different configurations from one another).

Further, the applications 102 and 103 can be, for example, desktop applications that can be used by desktop users and/or mobile applications that can be used by mobile device users. Although not shown in FIG. 1, each of the applications 102 and 103 (or similar applications) is executed on a terminal device, including but not limited to a personal, notebook or workstation computer, a kiosk, a PDA (personal digital assistant), a mobile phone or handset, another information terminal, etc., that can communicate with other devices through the network 104, which can be, for example, the Internet.

Figure 3:
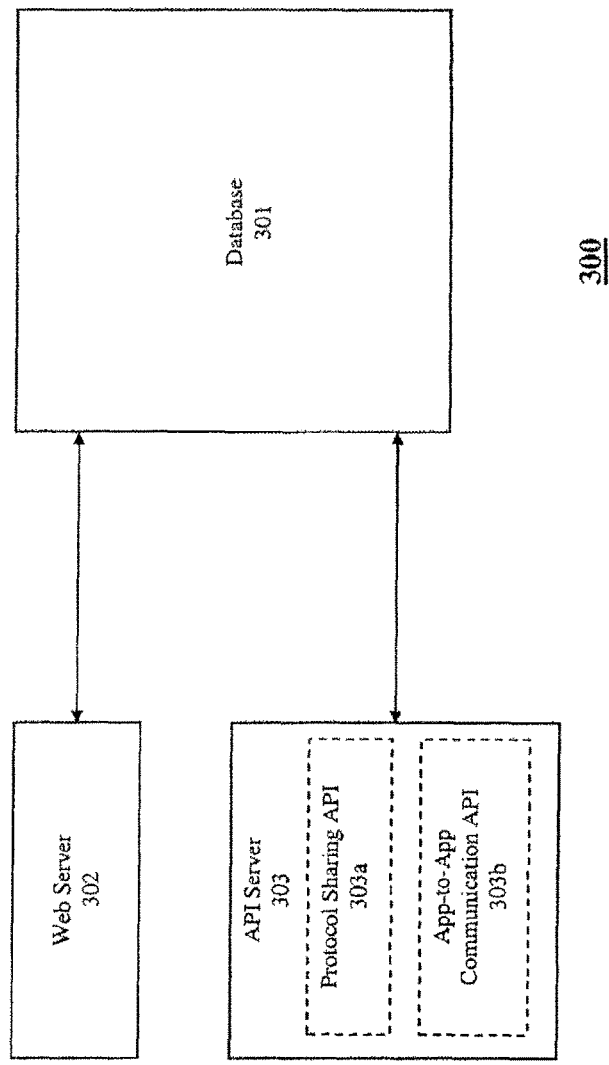
FIG. 3 shows a block diagram of a system, according to another exemplary embodiment.

By way of the aforementioned features of the repository 101 and the applications 102 and 103, the system 100 of FIG. 1 provides scientists and lab workers with the ability to structure the protocols for their experiments, reduce errors through interfacing with laboratory equipment, keep the protocols up to date, discover new protocols, connect with scientists working on similar projects and/or facilitate scientific collaboration. For example, as discussed above, scientists may use the application to track their progress throughout experiments in a form of protocols that are lists of steps with instructions. Scientists can also enter annotations, save protocols to the local device (thus using the application as a digital lab notebook), and/or share with other scientists without uploading to the centralized repository or submit the protocols to the centralized repository. Submitting a protocol to the centralized repository may be viewed as essentially publishing the protocol for the community. Once published, other scientists will be able to download protocols to their own devices and use them. Scientists can change an existing protocol if they discover imperfections in the original. The applications 102 and 103 may communicate with the cloud based centralized repository 101 and between each other via a set of proprietary APIs (e.g. ZappyLabAPI), for example, located on an API server 303 shown in FIG. 3. The repository has a web-based interface for allowing users to view submitted protocols, search by keyword or protocol features as well as discover and communicate with other scientists.

Preferably, no user login or any other credentials are required to use the mobile application. However, in order to submit or access protocols in the repository users may be required to register by providing basic personal information such as their name, location and field of research.

Figure 4:
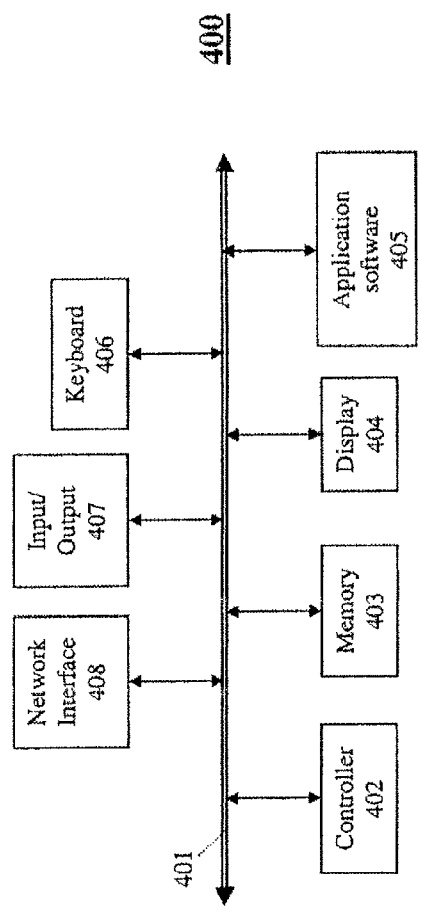
FIG. 4 shows a block diagram of an exemplary configuration of a terminal for running applications shown in FIG. 1.

An example of a configuration of a terminal on which the applications 102 and 103 of FIG. 1 may run is shown schematically in FIG. 4. In FIG. 4, computer 400 includes a controller (or central processing unit) 402 that communicates with a number of other components, including memory 403, display 404, keyboard (and/or keypad) 406, other input/output (such as mouse, touchpad, stylus, microphone and/or speaker with voice/speech interface and/or recognition software, etc.) 407, network interface 408 and application software 405, by way of an internal bus 401.

The memory 403 can provide storage for program and data, and may include a combination of assorted conventional storage devices such as buffers, registers and memories [for example, read-only memory (ROM), programmable ROM (PROM), erasable PROM (EPROM), electrically erasable PROM (EEPROM), static random access memory (SRAM), dynamic random access memory (DRAM), non-volatile random access memory (NOVRAM), etc.].

The network interface 408 provides a connection (for example, by way of an Ethernet connection or other network connection which supports any desired network protocol such as, but not limited to TCP/IP, IPX, IPX/SPX, or NetBEUI) to network 401.

Application software 405 is shown as a component connected to the internal bus 401, but in practice is typically stored in storage media such as a hard disk or portable media, and/or received through the network 401, and loaded into memory 403 as the need arises.

Depending on the type of the particular terminal device, one or more of the components shown in FIG. 4 may be missing. For example, a particular mobile phone may be missing the keyboard 406.

Additional aspects or components of the computer 400 are conventional (unless otherwise discussed herein), and in the interest of clarity and brevity are not discussed in detail herein. Such aspects and components are discussed, for example, in "How Computers Work", by Ron White (Quo Corporation 1999), and "How Networks Work", by Frank J. Derfler, Jr. and Les Freed (Que Corporation 2000), the entire contents of each of which are incorporated herein by reference.

Figure 6:
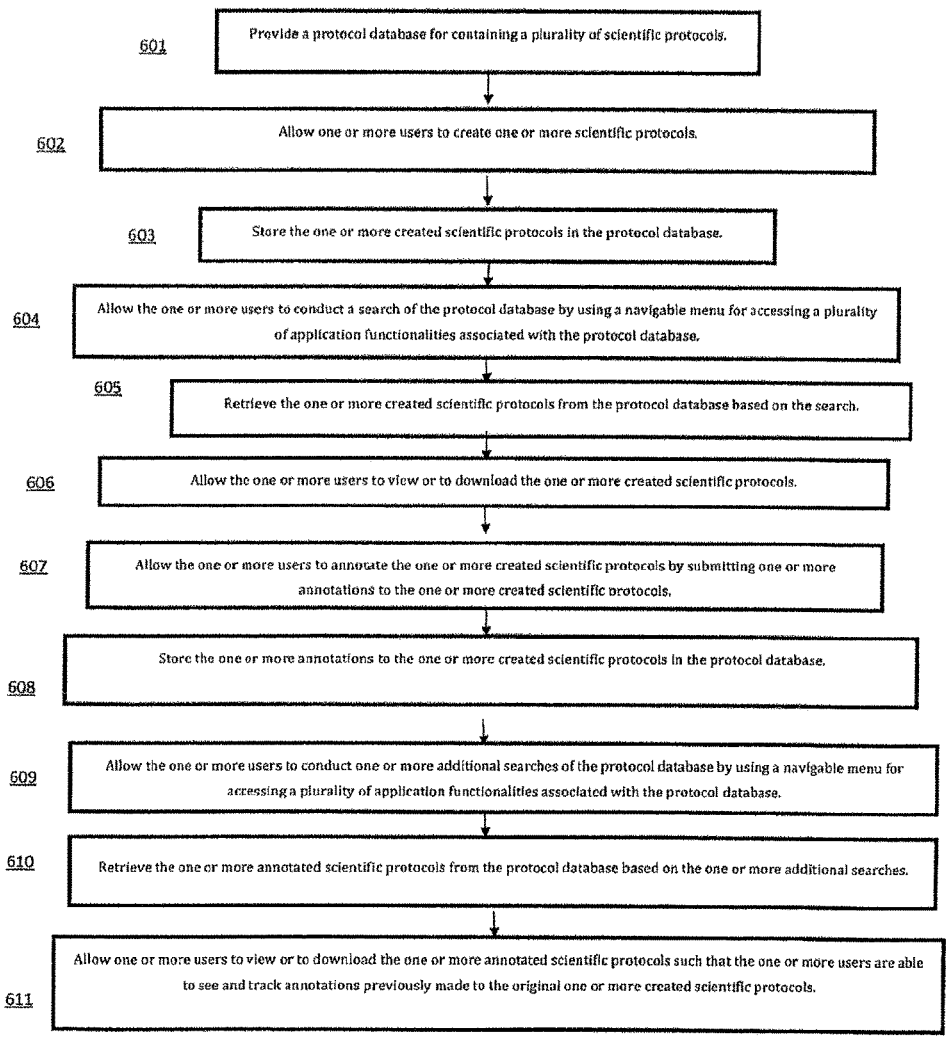
FIG. 6 shows a flow-chart illustrating a processor-implemented method for providing a web-based repository of science protocols according to an exemplary embodiment.

FIG. 6 shows a flow-chart illustrating a processor-implemented method for providing a web-based repository of science protocols according to one embodiment. Step 601 comprises providing a protocol database for containing a plurality of scientific protocols. The protocol database may be web-based. Step 602 comprises allowing one or more users to create one or more scientific protocols. Creating one or more scientific protocols may comprise using a user interface to input information relating to one or more steps of an experiment, including step number, step name, duration, reagent, amount, description, a warning, and/or a reminder. Step 603 comprises storing the one or more created scientific protocols in the protocol database. Step 604 comprises allowing the one or more users to conduct a search of the protocol database by using a navigable menu for accessing a plurality of application functionalities associated with the protocol database. According to an embodiment, conducting a search may be based on specified keywords and/or search options such as reagents, a type of protocol, and/or a scientific domain. Step 605 comprises retrieving the one or more created scientific protocols from the protocol database based on the search. The retrieval of the one or more created scientific protocols may be recorded as a protocol instance, thus serving as a digital lab notebook. Step 606 comprises allowing the one or more users to view or to download the one or more created scientific protocols.

Step 607 comprises allowing one or more users to annotate the one or more created scientific protocols by submitting one or more annotations to the one or more created scientific protocols. Step 608 comprises storing the one or more annotations to the one or more created scientific protocols in the protocol database. According to an embodiment, each of the one or more annotations to the one or more created scientific protocols may be stored separately as additional entries associated with the one or more scientific protocols. In this way, the one or more annotated scientific protocols may be displayed to the one or more users in such a way as to show every single annotation made to a given scientific protocol by the one or more users along with originally created scientific protocol. Step 609 comprises allowing the one or more users to conduct one or more additional searches of the protocol database by using a navigable menu for accessing a plurality of application functionalities associated with the protocol database. Step 610 comprises retrieving one or more annotated scientific protocols from the protocol database based on the one or more additional searches. Step 611 comprises allowing one or more users to view or download the one or more annotated scientific protocols from the protocol database. According to an embodiment, the one or more users are able to see and track annotations previously made to the original one or more created scientific protocols.

According to another embodiment, the one or more users may be able to modify and/or annotate the one or more created scientific protocols to create one or more modified scientific protocols. Such embodiment may comprise storing separately in the protocol database both the original one or more created scientific protocols and the one or more modified scientific protocols. Such embodiment may further comprise allowing one or more users to conduct one or more additional searches of the protocol database, and retrieving the one or more modified scientific protocols and/or the original one or more scientific protocols from the protocol database. The embodiment may further comprise allowing one or more users to view or download the one or more modified scientific protocols and/or the original one or more created scientific protocols. According to this embodiment, the one or more users may have the option to view either the original created scientific protocol or any one of the modified versions of the scientific protocol.

According to another embodiment, the one or more users may be able to modify and/or annotate the one or more created scientific protocols to overwrite the original one or more created scientific protocols to create one or more modified scientific protocols. Such embodiment may comprise storing in the protocol database the one or more modified scientific protocols by replacing the original one or more created scientific protocols with the one or more modified scientific protocols. Such embodiment may further comprise allowing one or more users to conduct one or more additional searches of the protocol database, and retrieve the one or more modified scientific protocols from the protocol database. Such embodiment may further comprise allowing one or more users to view or to download the one or more modified scientific protocols.

According to an embodiment, a protocol management application may be allowed to communicate with a lab device (e.g., to monitor a status of the lab device, to monitor a setting of the lab device, and/or to automatically configure a setting of the lab device) based on the one or more created scientific protocol and/or based on the one or more modified scientific protocol. The method may include allowing a protocol management application to communicate with a lab device to automatically configure the lab device based on the one or more created scientific protocols and/or annotated scientific protocols and/or modified scientific protocols. In some embodiments, the method may include allowing a protocol management application to communicate with a lab device to monitor a status of the lab device based on the one or more created scientific protocols and/or annotated scientific protocols and/or modified scientific protocols. Some of the advantages of the present disclosure, which are not: limited to those provided hereinafter, include:

(1) revolutionized scientific laboratory practice and more efficient research due to ready availability of a user-populated protocol repository (2) a new venue for researchers to share new method findings (3) a new structure to assign credit to scientists who improve and modify existing protocols;

(4) minimization of experimental procedure errors through communication between the user's mobile or desktop device and laboratory equipment.

The above-mentioned embodiments and examples are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A protocol management apparatus including a processor and a non-transitory storage medium embodying instructions executable by the processor to configure the protocol management apparatus to include:
   a creation part configured to provide a protocol creation user interface, receive a series of user inputs entered by the user through the protocol creation user interface, create a new protocol based on the series of user inputs, and add the new protocol to a local protocol database;
   a modification part configured to provide a protocol modification user interface, receive a user selection of a specific protocol of the plurality of protocols and a series of user inputs entered by the user through the protocol modification user interface, and modifying the specific protocol based on the series of user inputs;
   an output part configured to provide a protocol output user interface, receive a user selection of a specific protocol of the plurality of protocols and a destination specified by the user, and output the user selected protocol to the specified destination to allow for execution of the user selected protocol, the user selected protocol including a particular step amongst one or more steps of the user selected protocol that specifies a desired setting of a lab device amongst one or more lab devices during execution of the particular step;
   a display part configured to display the user a list of the plurality of protocols stored in the local protocol database; and
   a lab device interface part configured to allow for execution of the user selected protocol by interfacing the user selected protocol with the lab device amongst the one or more lab devices, the lab device interface part determining, when the particular step of the user selected protocol is reached during execution of the selected protocol, whether the desired setting of the lab device specified in the particular step corresponds to an actual setting of the lab device, wherein, when it is determined that the actual setting of the lab device does not correspond to the desired setting of the lab device specified in the particular step, the lab device interface part causes a warning message to be displayed on the display part before the particular step is executed, the warning message indicating that the actual setting of the lab device does not correspond to the desired setting specified in the particular step,
   wherein the display part is configured to display a checklist of all of the one or more steps included in the user selected protocol, allow a user to check off each step in the user selected protocol that is completed, and alert the user when it is time to move on to the next step.

2. The apparatus of claim 1, wherein the protocol creation user interface allows the user to create a new protocol by inputting one step at a time, each step including one of a sequential step number, a step name, a duration, a reagent, an amount, a description, a warning or reminder.

3. The apparatus of claim 1, wherein the user is permitted to import, using a text file or e-mail, a protocol to be registered as a new protocol in the local protocol database, and the text file is a comma-separated values (CSV) file.

4. The apparatus of claim 1, wherein the display part displays a navigable menu including a plurality of menu items including either a list of one or more protocols stored in the local protocol database or another navigable menu.

5. The apparatus of claim 1, wherein the protocol modification user interface provides the user with a text field for receiving an annotation for a specified step of the specified protocol.

6. The apparatus of claim 1, wherein when the display part receives a user selection of a specified protocol, the display part displays the protocol to the user, including each step of the protocol and annotations and corresponding to said each step.

7. The apparatus of claim 1, wherein the lab device interface part is configured to communicate step-specific settings to the lab device to automatically configure the lab device based on the step-specific settings.

8. The apparatus of claim 1, wherein the lab device interface part is configured to communicate with the lab device to monitor a status of the lab device,
   wherein, when the status of the lab device is changed, the lab device interface part causes a message to be displayed on the protocol management apparatus, indicating that the status of the lab device has been changed.

* * * * *